US00PP29233P3

(12) United States Plant Patent
Probst

(10) Patent No.: US PP29,233 P3
(45) Date of Patent: Apr. 10, 2018

(54) ***COREOPSIS* PLANT NAMED 'PROMON'**

(50) Latin Name: ***Coreopsis hybrida*/Tickseed Plant**
Varietal Denomination: Promon

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 141 days.

(21) Appl. No.: 14/757,512

(22) Filed: Dec. 23, 2015

(65) Prior Publication Data

US 2017/0188503 P1 Jun. 29, 2017

(51) Int. Cl.
*A01H 5/02* (2006.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

The present *Coreopsis* variety was created during a controlled plant breeding program. A compact and bushy growth habit is displayed. Attractive, yellow daisy-type inflorescences with a burgundy eye zone particularly during cooler growing conditions are formed. The dark green foliage coloration contrasts nicely with the blossom coloration. Excellent resistance to powdery mildew has been displayed during observations to date. The plant is a perennial and has been observed to be hardy to at least U.S.D.A. Hardiness Zone No. 5. The plant can be grown to advantage as attractive ornamentation in parks, gardens, and residential settings.

1 Drawing Sheet

Botanical/commercial classification: *Coreopsis hybrida*/Tickseed Plant.

Varietal denomination: cv. Promon.

SUMMARY OF THE INVENTION

Plants of *Coreopsis* sometimes bear a common name such as Tickseed, and are recognized to be ornamental herbaceous plants for landscape or container uses.

The new variety of *Coreopsis* hybrid was created from an ongoing controlled breeding program in 2010 in Hubbardston, Mass., U.S.A. The objective of the breeding program was to develop new varieties having superior attributes that are long-lived, exhibit a perennial habit to at least U.S.D.A. Hardiness Zone No. 5, and display an array of attractive flower colorations and plant forms. The female parent (i.e., the seed parent) of the new variety was an unnamed, unreleased, and non-patented *Coreopsis* plant designed Q2 09-7. Pollen used for the cross was pooled from a mixture of unnamed, unreleased, and non-patented *Coreopsis* plants that displayed limited fertility with the formation of a limited quantity of pollen. The exact male parent that contributed to the origin of the new variety is unknown.

It was found that the new *Coreopsis* plant displays the following combination of characteristics:

(a) displays a compact and bushy growth habit,
(b) displays attractive bright yellow flowers with a burgundy eye zone particularly during cooler growing conditions,
(c) exhibits excellent resistance to powdery mildew, and
(d) is hardy to at least U.S.D.A. Hardiness Zone No. 5.

The expressed combination of characteristics enables the new cultivar to be readily distinguished from the 'Full Moon' variety (U.S. Plant Pat. No. 19,364) which also forms large clear yellow flowers. However, unlike the 'Full Moon' variety, the new variety displays a burgundy flower eye zone under cooler growing conditions, a more compact growth habit, and better resists mildew.

Additionally, the new variety can be readily distinguished from its ancestors. More specifically, the female parent (i.e., the seed parent), *Coreopsis* plant designed Q2 09-7, displays white flowers with a rose-purple edge and no eye, and is also very fertile producing an abundance of seeds; whereas the new variety displays yellow colored flowers and is sterile.

The new variety can be grown in the ground or in a container to provide attractive ornamentation in parks, gardens, and residential settings.

Asexual reproduction of the new variety in a controlled environment by the rooting of vegetative cuttings has been conducted at West Grove, Pa., U.S.A. It has been demonstrated that the combination of characteristics of the new variety is firmly fixed and is well retained in succeeding generations. Accordingly, the new variety can be asexually reproduced in a true-to-type manner. The new variety also can be asexually propagated by division.

The new cultivar has been named 'Promon'.

BRIEF DESCRIPTION OF THE PHOTOGRAPH

The accompanying photograph illustrates a typical flowering plant of the new variety at an age of approximately two years. The plant had been asexually reproduced by the use of vegetative cuttings and was growing outdoors on its own roots in the ground in full sun during June at West Grove, Pa., U.S.A. The attractive yellow (with some burgundy at the eye zone) blossoms combined with a compact and bushy growth habit are shown.

DETAILED BOTANICAL DESCRIPTION

The chart used in the identification of the colors described herein is The R.H.S. Colour Chart of The Royal Horticultural Society, London, England (1995 Edition or equivalent). The plants had been asexually reproduced by the rooting of vegetative cuttings, were approximately one year of age, and were observed during June while growing outdoors in the ground in full sun at West Grove, Pa., U.S.A.

Botanical classification: *Coreopsis hybrida.*

Cultivar: Promon.

Plant:

*Habit.*—Vigorous herbaceous perennial, compact and bushy, clump-forming with sturdy stems and an upright and spreading canopy.

*Height.*—Approximately 30 to 45 cm on average. This compares to approximately 70 to 75 cm on average for the 'Full Moon' variety.

*Width.*—Approximately 50 to 70 cm on average. This compares to approximately 100 cm on average for the 'Full Moon' variety.

*Branching.*—Highly branched, commonly with approximately 9 basal branches on average and approximately 20 secondary branches on average.

*Branch internodes.*—Arise opposite at nodes, variable, and typically approximately 3 cm in length.

*Stem shape.*—Substantially round and wiry.

*Stem length.*—Main stems commonly are approximately 15 cm in length on average with laterals of approximately 7 cm in length (excluding peduncles).

*Stem diameter.*—Main stems commonly are approximately 6 mm in diameter on average.

*Stem texture.*—Smooth.

*Stem color.*—Near Green Group 137A.

*Roots.*—Fibrous, fine, and well branched.

Foliage:

*Arrangement.*—Opposite, single, sessile.

*Configuration.*—Simple with trifid upper leaves, narrow lanceolate.

*Length.*—Variable, up to approximately 10 cm in length for entire leaves, and up to approximately 7 cm in length for trifid leaves, secondary lobes commonly average approximately 5 cm in length on average.

*Width.*—Variable, and up to 10 mm in width for entire leaves, and up to approximately 3 cm in width for trifid leaves, secondary lobes commonly average approximately 5 mm in width on average.

*Apex.*—Acute.

*Base.*—Attenuate.

*Margin.*—Entire with short pubescence.

*Texture.*—Very finely pubescent on the upper and under surfaces.

*Venation.*—Non-conspicuous, pinnate, and of substantially the same coloration as the foliage on both surfaces.

*Color.*—Young leaves: near Green Group 137A on the upper surface, and near Green Group 137B on the under surface. Mature leaves: near Green Group 137A on the upper surface, and near Green Group 137B on the under surface.

Flower description:

*Quantity.*—When grown in a one-gallon container commonly 75 flowers are displayed at a time.

*Bud shape.*—Generally spherical.

*Bud size.*—Approximately 5 mm in length and diameter on average.

*Bud color.*—Grey-Brown Group 199C, and covered with bracts of Yellow-Green Group 147B.

*Flower appearance.*—Large daisy-type composite inflorescence form with elongated oblong-shaped ray florets and disc florets at the center forming a radiant head. Inflorescences are borne on terminals arising from leaf axils.

*Lastingness.*—Commonly approximately one week until senescence of ray florets while disc florets and bracts tend to be persistent.

*Flowering response.*—Under normal conditions, plants flower from June to August in southeastern Pennsylvania, U.S.A.

*Inflorescence diameter.*—Commonly up to about 6.3 cm on average when fully open.

*Inflorescence depth.*—Commonly up to approximately 1.2 cm on average when open.

*Disc.*—Commonly up to approximately 1.3 cm in diameter on average.

*Fragrance.*—Slightly acrid when crushed.

*Ray florets.*—Aspect: held slightly cupped upward when opening and becoming nearly horizontal at maturity. Shape: broadly oblanceolate. Length: approximately 2.7 cm on average. Width: approximately 1.8 cm on average. Apex: broadly acute. Base: cuneate. Margin: emarginated with three notches. Texture: smooth, velvety on both surfaces, and sterile. Number: approximately eight arranged in a single whorl. Color: on the upper surface when opening and when mature near Yellow Green-Yellow Group 1A, and on the under surface when opening and when mature near Green-Yellow Group 1B.

*Disc florets.*—Arrangement: massed at the center of the inflorescence. Shape: tubular, fused at the base, and flared at the apex. Length: commonly approximately 8 mm on average. Width: commonly approximately 1.1 mm on average at the base. Color: primarily near Greyed-Orange Group 163B when immature, near Yellow Group 5C when fully open, becoming Greyed-Orange Group 165B when dried as the ray florets drop. The base is near Yellow Group 5C with a flared portion of near Yellow Group 5A.

*Reproductive organs.*—Location: androecium and gynoecium present only among disc florets. Stamen number: five per floret fused into a tube surrounding the style. Anther size: approximately 3 mm in length on average and approximately 0.4 mm in width on average. Anther color: near Greyed-Orange Group 165B. Pollen quantity: moderately produced during observations to date. Pistil number: one per floret. Pistil length: approximately 6 mm on average. Style appearance: very fine. Style color: near Yellow-Green Group 154D and somewhat translucent. Stigma shape: bifid and pilose, with recurved branches approximately 1 mm in length. Stigma color: commonly near Yellow-Orange Group 17A. Ovary size: commonly approximately 1.5 mm in length on average, and approximately 1 mm in width on average. Ovary color: near Yellow-Green Group 154D. Receptacle size: approximately 8 mm in length on average and approximately 1.2 cm in diameter on average. Receptacle color: near Yellow-Green Group 154D. Seeds/fruit: none encountered during observation to date.

*Involucral bracts.*—Number commonly in two rows of eight. Arrangement: the outer bracts are unfused and somewhat reflexed when the flower is fully open and becoming substantially horizontal after the ray florets drop. The inner bracts surround the receptacle in a cam panulate form with the apical portion unfused and spreading and held close to the ray florets. Shape: entire on the inner and outer bracts. Size: outer bracts commonly up to 5 mm in length and 3 mm in width at the widest point, and inner bracts approximately 1 cm in length and 5 mm in width with a free portion approximately 5 mm in length and approximately 3 mm in width. Apex: acute on the inner and outer bracts. Texture: somewhat waxy on the inner bracts and the outer bracts are smooth and covered with short pubescence. Margins: entire on the inner and outer bracts. Color: outer bracts are near Green Group 1378 on both surfaces, the fused portion of the inner bracts is near Yellow-Green Group 148A, the unfused portion of the inner bracts is near Yellow-Green Group 152B on both surfaces, and the center, apex and margin are near Yellow-Green Group 152B.

*Peduncles*.—Strength: relatively strong. Size: commonly approximately 11 cm in length on average, and approximately 2 mm in diameter on average. Texture: glabrous. Color: commonly near Green Group 137B.

Disease resistance: Excellent with respect to powdery mildew during observations to date, including resistance to *Sphaerotheca macularis*. The 'Full Moon' variety has been observed to exhibit a lesser resistance to powdery mildew under the same growing conditions.

Hardiness: Hardy to at least U.S.D.A. Hardiness Zone No. 5 during observations to date.

Propagation: Through the rooting of vegetative cuttings, or by division. Plants of the new 'Promon' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Coreopsis* plant having the following combination of characteristics:

(a) displays a compact and bushy growth habit, (b) displays attractive bright yellow flowers with a burgundy eye zone particularly during cooler growing conditions, (c) exhibits excellent resistance to powdery mildew, and (d) is hardy to at least U.S.D.A. Hardiness Zone No. 5;

substantially as illustrated and described.

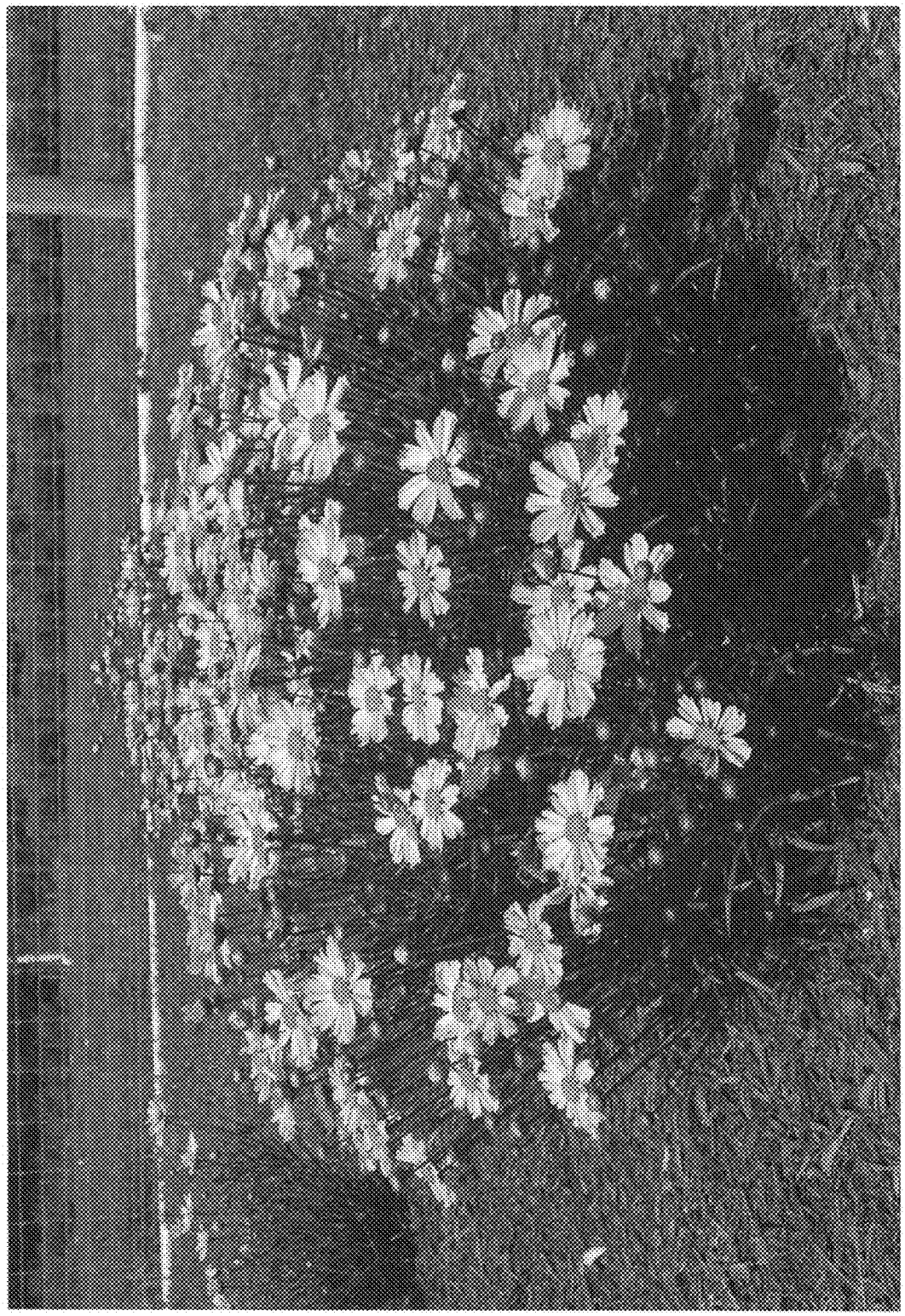

* * * * *